United States Patent
Tanaka

(10) Patent No.: US 8,444,553 B2
(45) Date of Patent: May 21, 2013

(54) ENDOSCOPE APPARATUS HAVING A BENDING DRIVING CONTROL SECTION FOR CONTROLLING A MOTION OF A DISTAL OF A BENDING PORTION

(75) Inventor: Hideki Tanaka, Tami (JP)

(73) Assignee: Olympus Medical Systems Corp., Tokyo (JP)

( * ) Notice: Subject to any disclaimer, the term of this patent is extended or adjusted under 35 U.S.C. 154(b) by 159 days.

(21) Appl. No.: 12/983,965

(22) Filed: Jan. 4, 2011

(65) Prior Publication Data

US 2011/0275892 A1    Nov. 10, 2011

Related U.S. Application Data

(63) Continuation of application No. PCT/JP2010/061589, filed on Jul. 8, 2010.

(30) Foreign Application Priority Data

Aug. 26, 2009    (JP) .................................. 2009-195865

(51) Int. Cl.
   *A61B 1/005*    (2006.01)
(52) U.S. Cl.
   USPC ......................................... 600/146; 600/145
(58) Field of Classification Search
   USPC ................. 600/117, 118, 137, 145, 146, 152, 600/173
   See application file for complete search history.

(56) References Cited

U.S. PATENT DOCUMENTS

| | | | |
|---|---|---|---|
| 4,941,456 A * | 7/1990 | Wood et al. | 600/152 |
| 5,060,632 A | 10/1991 | Hibino et al. | |
| 5,159,446 A * | 10/1992 | Hibino et al. | 348/65 |
| 5,243,967 A * | 9/1993 | Hibino | 600/109 |
| 5,609,563 A * | 3/1997 | Suzuki et al. | 600/118 |
| 2005/0154261 A1* | 7/2005 | Ohline et al. | 600/141 |
| 2007/0173694 A1* | 7/2007 | Tsuji et al. | 600/146 |
| 2008/0262311 A1* | 10/2008 | Itou et al. | 600/152 |
| 2010/0076263 A1* | 3/2010 | Tanaka et al. | 600/109 |

FOREIGN PATENT DOCUMENTS

| | | |
|---|---|---|
| JP | 03-268735 | 11/1991 |
| JP | 04-002320 | 1/1992 |
| JP | 04-002321 | 1/1992 |
| JP | 04-002322 | 1/1992 |
| JP | 05-211993 | 8/1993 |
| JP | 2005-279118 | 10/2005 |

OTHER PUBLICATIONS

International Search Report dated Aug. 24, 2010.

* cited by examiner

*Primary Examiner* — John P Leubecker
(74) *Attorney, Agent, or Firm* — Scully, Scott, Murphy & Presser, P.C.

(57) ABSTRACT

An endoscope apparatus includes an insertion portion to be inserted into a subject, a bendable bending portion provided in a distal end side of the insertion portion, a bending driving section that drives the bending of the bending portion, and a bending driving control section that controls the bending driving section based on an inputted control signal to cause a distal end of the bending portion to make a turning motion with respect to a proximal end thereof.

15 Claims, 10 Drawing Sheets

FIG.6
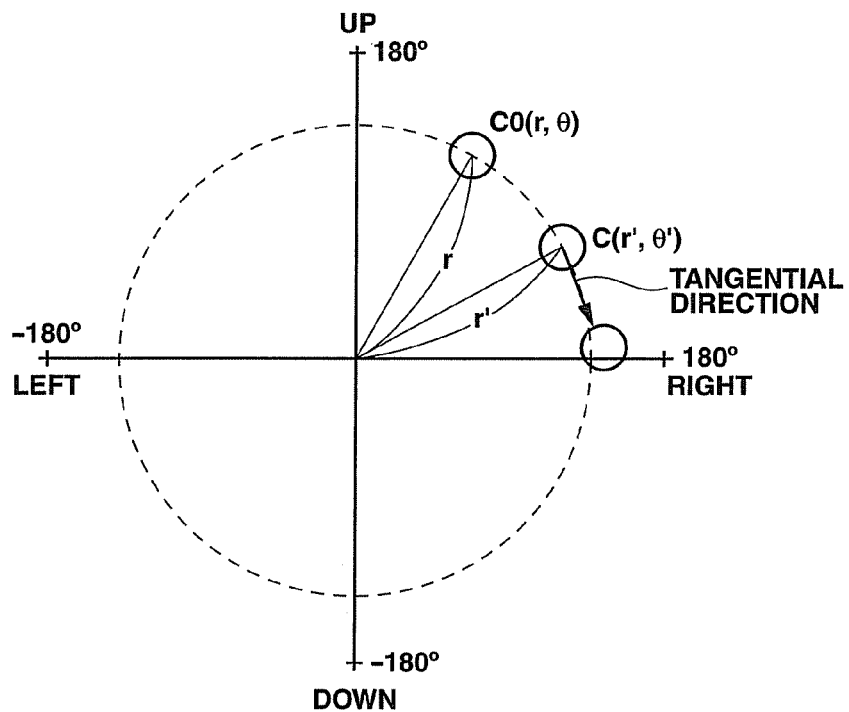
FIG.7
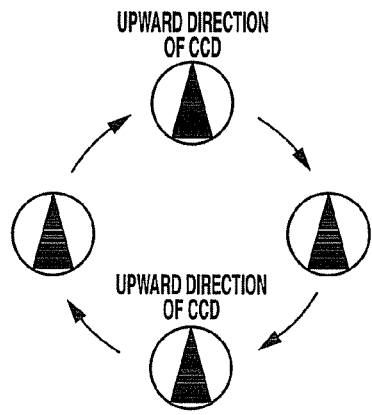
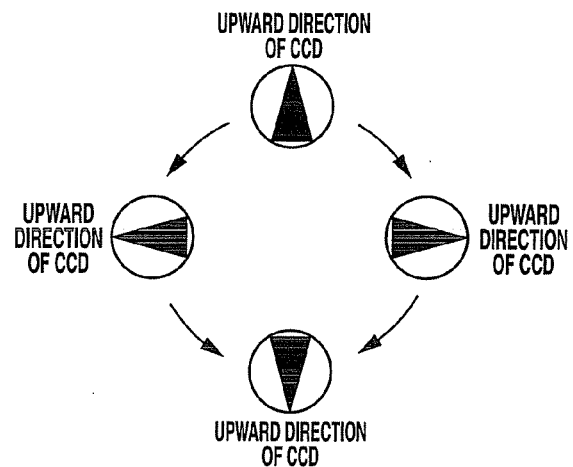

ENDOSCOPE APPARATUS HAVING A BENDING DRIVING CONTROL SECTION FOR CONTROLLING A MOTION OF A DISTAL OF A BENDING PORTION

CROSS REFERENCE TO RELATED APPLICATION

This application is a continuation application of PCT/JP2010/061589 filed on Jul. 8, 2010 and claims benefit of Japanese Application No. 2009-195865 filed in Japan on Aug. 26, 2009, the entire contents of which are incorporated herein by this reference.

BACKGROUND OF THE INVENTION

1. Field of the Invention

The present invention relates to an endoscope apparatus which is configured to drive the bending of a bending portion provided in the vicinity of a distal end of an insertion portion.

2. Description of the Related Art

In recent years, endoscopes which are provided with a bendable bending portion in the vicinity of the distal end of an insertion portion have come to be widely used in the medical field and so on. Providing a bending portion on the distal end side of the insertion portion makes it easy to smoothly insert the insertion portion into a curved body cavity.

Moreover, for insertion from an anus to the deep side of a large intestine, there is a technique in which an operator performs operation to twist the proximal end side of the insertion portion around the axis of the insertion portion so that by this twisting operation, the distal end side of the insertion portion is inserted by being twisted as well.

It is noted that Japanese Patent Laid-Open Publication No. 2005-279118 discloses an endoscope apparatus, in which the distal end side of the insertion portion is configured to be bendable (curvable), and a twisting mechanism for twisting the insertion portion around its axis is provided.

SUMMARY OF THE INVENTION

An endoscope apparatus relating to the present invention includes:
an insertion portion that is inserted into a subject;
a bending portion provided on a distal end side of the insertion portion, the bending portion being bendable and turnable centering around an insertion axis of the insertion portion;
a bending driving section that drives bending of the bending portion with respect to the insertion axis;
a bending driving control section that controls a bending driving status of the bending driving section based on a first or a second control signal to be inputted;
a bent shape maintaining section that detects bending driving information showing a bent shape of the bending portion according to control of the bending driving control section, and outputs the first control signal for controlling the bending driving section to the bending driving control section such that a bending driving status of the bending driving section according to the bending driving information is maintained; and
a bending direction changing section that outputs the second control signal to the bending driving control section, the second control signal adapted to continuously change a bending direction of the bending portion by controlling the driving of the bending driving section such that a distal end of the bending portion makes a turning motion forming a circular trail centering around the insertion axis, the bending portion maintaining a bent shape based on the first control signal outputted from the bent shape maintaining section.

BRIEF DESCRIPTION OF THE DRAWINGS

FIG. 6 is an explanatory diagram of the case where the bending portion is turned;

FIG. 7 is an explanatory diagram to show the difference between the cases where the bending portion is turned and twisted;

DETAILED DESCRIPTION OF THE PREFERRED EMBODIMENTS

Hereafter, embodiments of the present invention will be described with reference to the drawings.

[First Embodiment]

Figure 1:
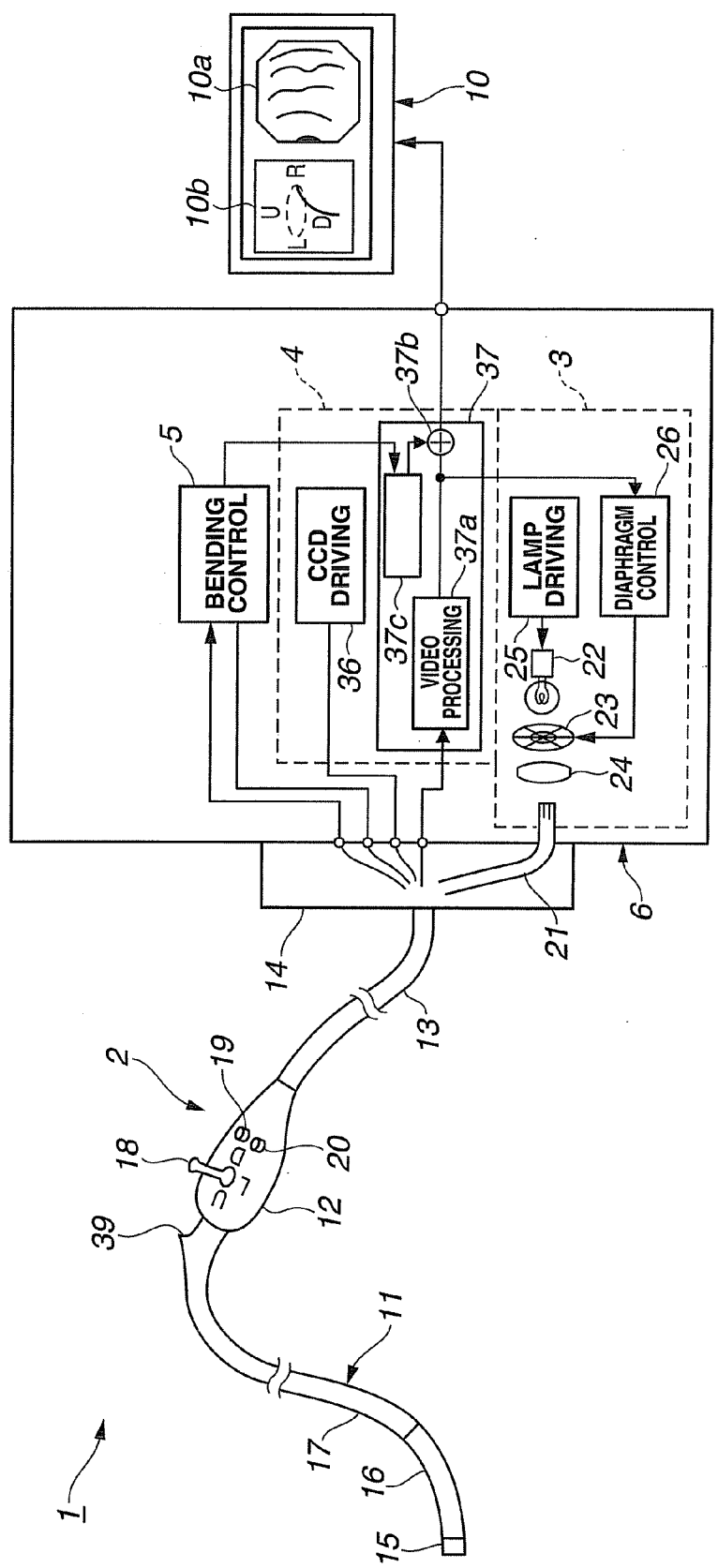
FIG. 1 is a diagram to show the general configuration of an endoscope apparatus of a first embodiment of the present invention.

As shown in FIG. 1, an endoscope apparatus 1 relating to a first embodiment of the present invention includes an endoscope 2 to be inserted into a body cavity, a light source portion 3 which is detachably connected with the endoscope 2 to provide illumination light thereto, a signal processing portion 4 which performs signal processing for image pickup means built in the endoscope 2, and a processor 6 having a built-in bending control section 5 that controls the bending, including turning motion, of a bending portion 16 of the endoscope 2.

Moreover, the endoscope apparatus 1 includes display means (a monitor 10 as a display device 9) for displaying an endoscope image corresponding to a video signal generated by the signal processing portion 4 within the processor 6.

The endoscope 2 includes an elongated insertion portion 11 which is to be inserted into a body cavity and is provided with the bendable bending portion 16 in the vicinity of a distal end thereof, an operation portion 12 which is provided in a rear end of the insertion portion 11, and a universal cord 13 which is extended from the operation portion 12. A connector 14 at the rear end of the universal cord 13 is detachably connected to the processor 6.

Moreover, the insertion portion 11 includes a rigid distal end portion 15 which is provided in a distal end thereof, a bending portion 16 which is provided adjacent to a rear end of the distal end portion 15, and a flexible tube portion 17 which has flexibility and extends from a rear end of the bending portion 16 to a front end of the operation portion 12.

The operation portion 12 is provided with a bending joystick 18 to be used by an operator such as a surgeon for performing instruction operation of a bending direction and a bending angle of the bending portion 16, a turning designation section 19 that makes up designating means (a designation section) for designating turning motion to turn a distal end portion side of the bending portion 16 with respect to the rear end (proximal end) of the bending portion 16, and a scope switch 20 for performing instruction operation of static images and so on.

Upon input of a signal or information associated with designation of turning motion from the turning designation section 19, the bending control section 5 controls bending driving means (a bending driving section) for driving the bending of the bending portion 16 so as to turn the bending portion 16. Then, designating means is formed by using the turning designation section 19 that designates turning motion to turn the distal end of the bending portion 16 with respect to the proximal end of the bending portion 16 by controlling the bending driving means for driving the bending of the bending portion 16.

A light guide 21 for transmitting illumination light is inserted through the inside of the insertion portion 11 of the endoscope 2 and so on, and a rear end of the light guide 21 serves an incident end surface protruding from a connector 14. Illumination light from a lamp 22 built in the light source portion 3 is incident onto the incident end surface via a diaphragm 23 and a condenser lens 24. It is noted that the lamp 22 is turned on by a lamp driving power supply supplied from a lamp driving circuit 25 thereby generating illumination light.

Moreover, the diaphragm 23 is subjected to the control of an opening amount (amount of aperture) by a diaphragm control circuit 26 for allowing illumination light to pass through.

The illumination light transmitted by the light guide 21 is emitted to the outside from a light guide distal end surface which is fixed to the distal end portion 15 of the insertion portion 11 further through an illumination lens 27 (see FIG. 2) attached to an illumination window and illuminates an affected part etc. in a body cavity.

Figure 2:
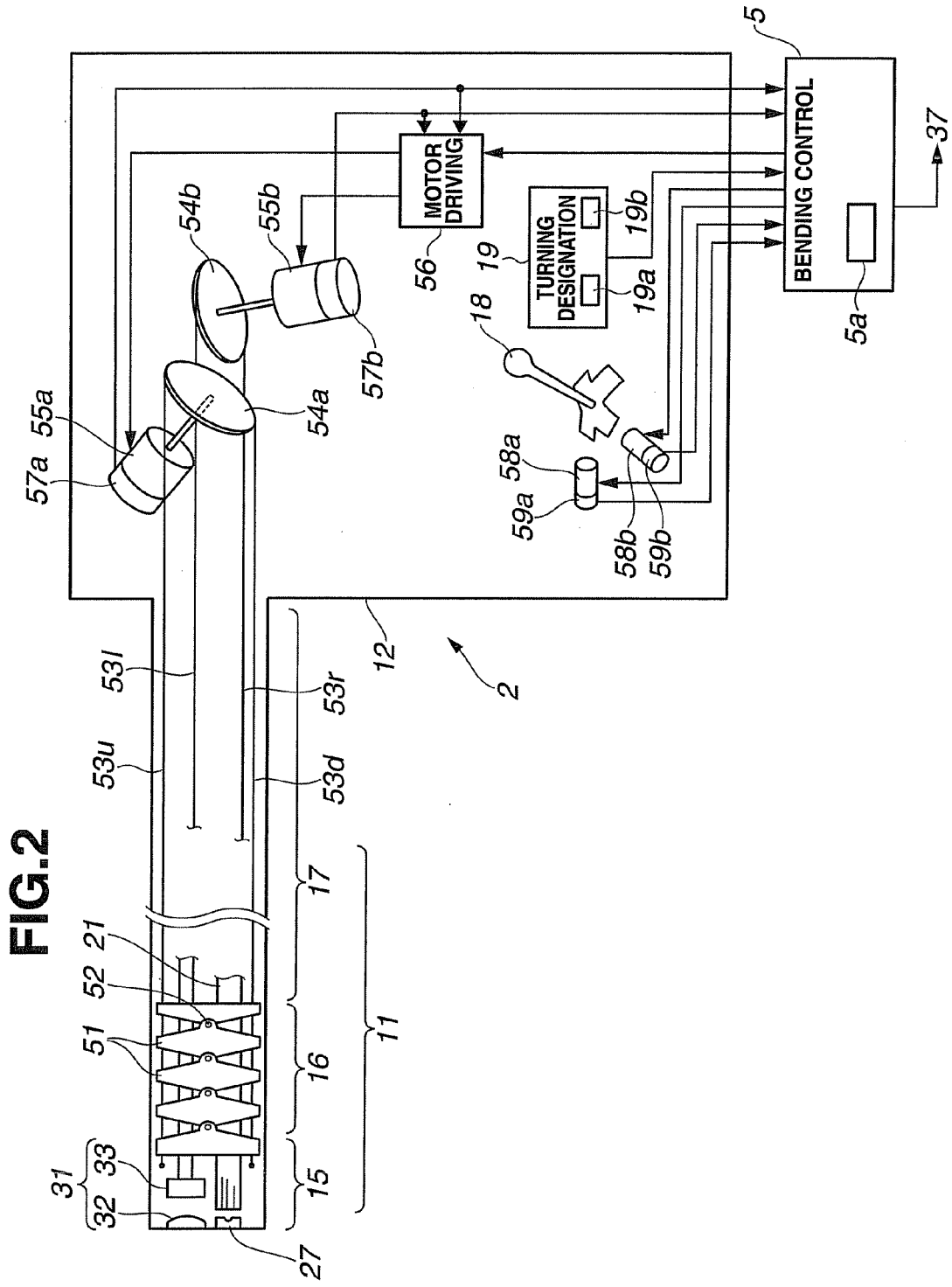
FIG. 2 is a schematic diagram to show the configuration to turn and bend a bending portion in an endoscope.

As shown in FIG. 2, an observation window is provided adjacent to the illumination window in the distal end portion 15. An image pickup unit 31 which makes up image pickup means is attached to the observation window.

The image pickup unit 31 includes an objective lens 32 attached to a lens frame and a charge coupled device (abbreviated as CCD) 33 as an image pickup device, the image pickup surface of which is disposed in an image forming position by the objective lens 32.

A cable, the distal end side of which is connected to the CCD 33, is inserted through the insertion portion 11 and so on and the rear end side thereof is connected to a CCD driving circuit 36 and a video circuit 37, which make up a signal processing portion 4 within the processor 6 shown in FIG. 1, through an electrical contact of the connector 14 shown in FIG. 1.

The CCD driving circuit 36 generates a CCD driving signal and applies the CCD driving signal to the CCD 33. The CCD 33 performs photoelectric conversion of an optical image formed on an image pickup surface by the application of a CCD driving signal, to output the signal as a CCD output signal (image pickup signal).

The CCD output signal is inputted into a video processing circuit 37a within a video circuit 37, and the video processing circuit 37a generates a video signal of an endoscope image picked up by the CCD 33, and the endoscope image is displayed in an endoscope display area 10a in a display screen of the monitor 10 via a mixer 37b which performs mixing.

Moreover, the video signal generated by the video processing circuit 37a is inputted into the diaphragm control circuit 26, and the diaphragm control circuit 26 calculates an average brightness, for example, by integrating a luminance signal component of the video signal at a predetermined period. The opening amount of the diaphragm 23 is adjusted with a differential signal, which is obtained by subtracting a reference value corresponding to an appropriate brightness from the signal of the average brightness, as a diaphragm control signal. Then, the amount of the illumination light which passes through the diaphragm 23 is automatically adjusted so as to be consistent with the reference value, by the diaphragm control signal.

Moreover, a bending portion shape generation circuit 37c, which generates a video signal representing a bent shape of the bending portion 16 when a turning motion is designated, is provided in the video circuit 37.

The bending portion shape generation circuit 37c generates a video signal representing a bent shape of the bending portion 16 by receiving input of information for determining a bent status of the bending portion 16 during turning motion from the bending control section 5, and outputs the video signal to the mixer 37b.

Then, a bent shape of the bending portion 16 during turning motion is displayed in an information display area 10b of turning motion (turning mode) in the display screen of the monitor 10 as display means, as shown in FIG. 1.

In the case of during turning motion, a surgeon can confirm the bent shape of the bending portion 16 during the turning motion by observing the monitor 10.

A treatment instrument channel not shown is provided within the insertion portion 11, and the rear end side of the treatment instrument channel is in communication with a treatment instrument insertion port 39 provided in the vicinity of a front end of the operation portion 12.

Moreover, the bending portion 16 is provided in the vicinity of the distal end of the insertion portion 11, and the bending control section 5 provided within the processor 6 is configured to perform the control of a bending driving mechanism as shown in FIG. 2.

A plurality of bending pieces 51, which make up the bending portion 16, respectively have portions adjoining in the longitudinal direction of the bending portion 16, which are rotatably connected with rivets 52.

While the bending direction of each bending piece 51 is determined by the position where the rivet 52 is provided, the rivets 52 are disposed, herein, alternately or conveniently in a periodic manner between horizontal positions and vertical positions so as to be bendable in the vertical direction and the horizontal direction.

It is noted that in FIG. 2, by way of simplification, only the rivets 52 which cause to bend the bending pieces in the vertical direction are shown. Moreover, angle wires $53u$ and $53d$, and $53l$ and $53r$ for causing bending in the vertical direction and the horizontal direction are inserted through the insertion portion 11, and the front ends of the angle wires $53u$ and $53d$, and $53l$ and $53r$ are securely fixed to the distal end portion 15.

Further, the rear ends of the angle wires 53*u* and 53*d*, and 53*l* and 53*r* are fixed to s pulley 54*a* for vertical bending and a pulley 54*b* for horizontal bending, which are disposed within the operation portion 12.

The both pulleys 54*a* and 54*b* are reversibly rotated by electric motors 55*a* and 55*b*, which make up bending driving means for performing electrical driving of bending. The electric motors 55*a* and 55*b* are driving by a motor driving signal by a motor driving section 56. The operation of the motor driving section 56 is controlled by the bending control section 5. It is noted that although the bending control section 5 has been described in FIG. 1 by way of a configuration example in which the bending control section 5 is provided within the processor 6, it may be provided in the endoscope 2, such as in the operation portion 12. Moreover, the motor driving section 56 may be configured to be provided within the bending control section 5.

The electric motors 55*a* and 55*b*, which are driven by a motor driving signal by the motor driving section 56, rotate the pulleys 54*a* and 54*b*, and the angle wires 53*u*, 53*d*, 53*l* and 53*r* are drawn by the rotation of the pulleys 54*a* and 54*b*, thereby driving the bending of the bending portion 16 in the drawing direction.

Thus, the motor driving section 56, the electric motors 55*a* and 55*b*, and so on make up bending driving means that electrically drives the bending of the bending portion 16, and the bending control section 5 controls the operation to drive the bending of the bending portion 16 by the bending driving means.

When the pulleys 54*a* and 54*b* are rotated, a drawing amount of the angle wires 53*u*, 53*d*, 53*l* and 53*r* is determined corresponding to the rotation angle of the pulleys 54*a* and 54*b*, and the bending portion 16 bends corresponding to the drawing amount.

Therefore, detecting the rotation angle of the electric motors 55*a* and 55*b* or the pulleys 54*a* and 54*b*, or the drawing amount (the amount of travel) of the angle wires 53*u*, 53*d*, 53*l* and 53*r* will enable the detection of the bending angle of the bending portion 16.

In the present embodiment, it is configured such that the bending angle of the bending portion 16 is detected via the rotational angle of the pulley 54*a*, 54*b*, for example, by a rotary encoders (also simply referred to as an "encoder") 57*a* and 57*b* attached to the shaft portions of the electric motors 55*a* and 55*b*.

That is, it is configured such that the rotational angle of the pulleys 54*a* and 54*b*, in other words, the bending angle of the bending portion 16 corresponding to the rotational angle of the pulleys 54*a* and 54*b* can be detected based on the output signal of the encoders 57*a* and 57*b*. Therefore, the encoders 57*a* and 57*b* forms bent shape detection means (a bent shape detection section) that detects a bent shape of the bending portion 16.

The detected signal (a detected value) of pulley angle or bending angle based on the output signal of the encoders 57*a* and 57*b* is inputted into a motor driving section 56. The motor driving section 56 receives input of an instructed direction of bending and an instructed value of bending angle by the joystick 18 as bending instruction operation means via the bending control section 5 (it is noted that the output signal of the encoders 57*a* and 57*b* is also inputted into the bending control section 5 to be used for the display of a bent shape in a turning mode).

Accordingly, the motor driving section 56 drives the electric motors 55*a* and 55*b* to rotate such that the detected value by the encoders 57*a* and 57*b* will follow (agree with) the instructed values.

It is configured such that the bending control section 5 provides an instructed value by the bending instruction operation means to the motor driving section 56, and the motor driving section 56 controls the electric motors 55*a* and 55*b* to rotate such that the detected value of the bending angle agrees with the instructed value, thereby causing the bending portion 16 to bent up to an instructed, predetermined bending angle.

As the result of a surgeon performing the operation of tilting in any vertical or horizontal bending direction with the joystick 18 as bending instruction operation means (a bending instruction operation section) provided in the operation portion 12, the tilted direction will provide an instructed direction of bending, and the tilted angle will provide an instructed value of vending angle.

By the surgeon performing the instruction operation to tilt the joystick 18 in any horizontal or vertical direction, a vertical direction joystick motor 58*a* and a horizontal direction joystick motor 58*b* are caused to rotate according to the tilted directions.

The rotational angle is detected (sensed) by the encoders 59*a* and 59*b*, and the detection signal of the encoders 59*a* and 59*b* is inputted into the bending control section 5 as information of bending direction, and an instructed value of bending angle.

It is noted that joystick motors 58*a* and 58*b* are controlled by the bending control section 5, and detection signals of the encoders 59*a* and 59*b* are inputted into the bending control section 5 as well.

Then, the bending control section 5 outputs information of bending direction and an instructed value of bending angle as the detection signal of encoders 59*a* and 59*b* to the motor driving section 56 thereby controlling the operation thereof.

Further, in the present embodiment, a turning designation section 19 that makes up designating means for designating a turning motion of the bending portion 16 is provided, and the signal or information designated by the turning designation section 19 is inputted to the bending control section 5.

The turning designation section 19 includes a direction switch 19*a* for designating a turning direction, and a turning switch 19*b* for starting/stopping (ON/OFF) a turning motion. The configuration may be such that the direction switch 19*a* and the turning switch 19*b* are combined into a single unit.

It is noted that although the above described turning designation section 19 is provided in the operation portion 12 of the endoscope 2, the configuration may be such that the turning designation section 19 that can designate a turning motion is provided in a front panel of the processor 6 shown in FIG. 1, and the like.

The bending control section 5, which receives input of a signal to designate a turning direction from the turning designation section 19, has a function of a determination section 5*a* as determination means for determining the bending driving direction (also referred to as driving direction) of the bending portion 16 such that the bending portion 16 is turned, based on the designation information of a designated turning motion. Then, the motor driving section 56 applies a driving signal corresponding to a driving direction determined by the determination section 5*a* to the electric motors 55*a* and 55*b*, and the electric motors 55*a* and 55*b* drive the bending of the bending portion 16 so as to be turned in the driving direction determined by the determination section 5*a*.

Thus, the bending control section 5 controls the turning motion in a turning mode for turning the bending portion 16.

Figure 3:
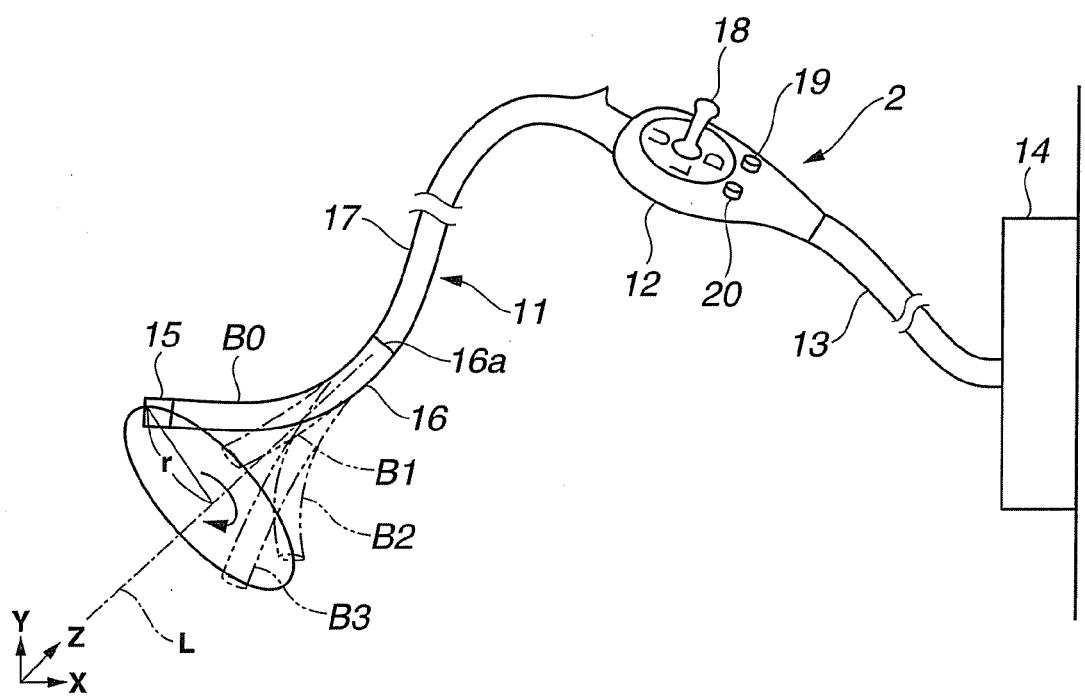
FIG. 3 is an explanatory diagram of a manner in which the bending portion is turned.

FIG. 3 is an explanatory diagram to show the shape, etc. of the bending portion 16 when subjected to a turning motion in a turning mode. The turning motion is a motion of the distal end or the distal end side of the bending portion 16 to turn in such a way to draw a circle about a proximal end 16a of the bending portion 16.

In this case, as seen from FIG. 3, the size of the circle drawn by the distal end of the bending portion 16, that is, the value of the turning radius will vary depending on the bending status of the bending portion 16. It is noted that the distal end of the bending portion 16 is herein used in the same meaning as the distal end of the distal end portion 15. Although, in a strict sense, the distal end of the distal end portion 15 is deviated by a length of the distal end portion from the distal end of the bending portion 16, the amount of the deviation is minor.

Moreover, the determination section 5a controls the driving operation by the motor driving section 56 to drive the bending portion 16 based on the determined information such as driving direction, etc.

It is noted that the driving direction for driving the bending of the bending portion 16 has a different meaning from a normal bending direction (or driving direction). When used to mean the bending direction to bend the bending portion 16, it is generally used to indicate the direction when the bending portion 16 is bent from a neutral state where it is not bent, and the bending angle is 0, to any vertical or horizontal direction.

In contrast to this, the driving direction to drive the bending of the bending portion 16 in a turning mode in the present embodiment is used to mean that the bending portion 16 is bent in such a way that the distal end of the bending portion 16 draws a circle clockwise or counterclockwise from a state of normal bending direction.

An axis L shown by a chain line in FIG. 3 shows the axis along the longitudinal axis of the bending portion 16 in a neutral state where the bending portion 16 is not bent, and the bending portion 16 lies on the axis L from the proximal end 16a of the bending portion 16 to the distal end side thereof in a neutral state.

Moreover, suppose that for example, a bent state B0 is a bent state in which a surgeon has turned on the turning switch 19b of the turning designation section 19. In this case, the distal end of the bending portion 16 in the bent state B0 is at a distance of a radius r from the axis L, and on a plane perpendicular to the axis L. As a result of a turning motion, the distal end of the bending portion 16 turns in such a way to draw a circular trail (that is, a turning circle) on the plane as shown in bent states B1, B2, and B3. Therefore, the above described radius r becomes a turning radius to make a turning motion. It is noted that the plane which is perpendicular to the axis L and in which the distal end of the bending portion 16 draws a circle is also referred to as a turning plane.

Moreover, setting the direction of the axis L to be the Z axis direction, the distal end of the bending portion 16 will be in X and Y planes as the turning planes each of which is perpendicular to the Z axis.

Next, the operation to turn the bending portion 16 according to the present embodiment will be described below. The power supply of the endoscope apparatus 1 is turned on and the endoscope apparatus 1 comes into an operating state.

A surgeon performs an endoscope inspection by inserting the insertion portion 11 of the endoscope 2 into the deep side of the large intestine from the anus of a patient. In a manipulation for insertion into the deep side of the large intestine, there is a scene where twisting operation is effective. For example, when the intestinal tract 60 of the large intestine is twisted (frequently occurs, particularly in a transition portion from the sigmoid colon to the descending colon) as shown in the left figure of FIG. 4, the twisted state is removed as shown in the right side of FIG. 4 by twisting the endoscope in the right direction while maintaining the bent state.

However, in such twisting operation:

(a) if the twisting speed is abrupt, the engagement between the distal end of the endoscope and the intestinal tract 60 is disengaged, resulting in a failure of the manipulation of insertion into the deep side;

(b) it is necessary to turn the endoscope by 180 degrees while grasping it, and therefore the amount of twisting operation tends to be insufficient when turning manipulation is performed only with the wrist; and (c) since the direction of observation by the endoscope is reversed, it is likely to erroneously recognize the direction of the distal end of the endoscope.

It is noted that when the above described conventional example is used, (c) cannot be solved, though there is possibility to solve (a) and (b).

Figure 4:
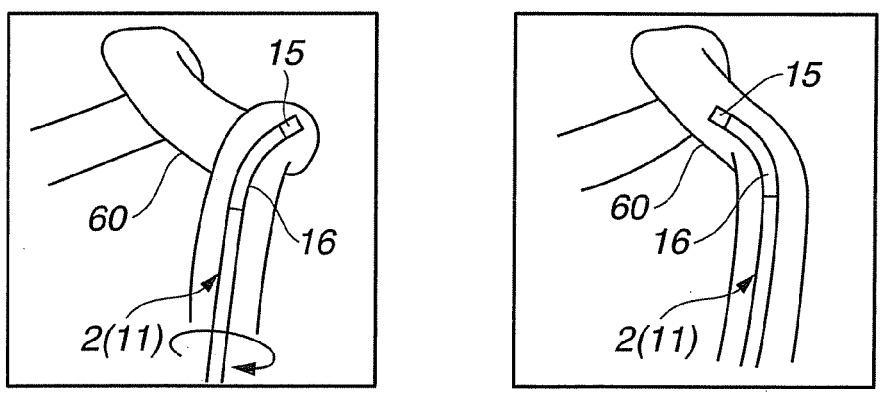
FIG. 4 is an explanatory diagram of a manner in which a distal end side of the insertion portion is inserted into a large intestine, and is twisted or turned thereby being inserted into the deep side thereof.

In contrast to this, the present embodiment can solve (c), which cannot be solved by the conventional example, by a turning motion as shown in FIG. 3 not by a twisting motion even for the case of FIG. 4, thereby enabling the smooth insertion of an endoscope into the deep side of the large intestine with simple operation. An example of control procedure when the distal end of the bending portion 16 is turned as described above will be described with reference to the flowchart of FIG. 5.

Figure 5:
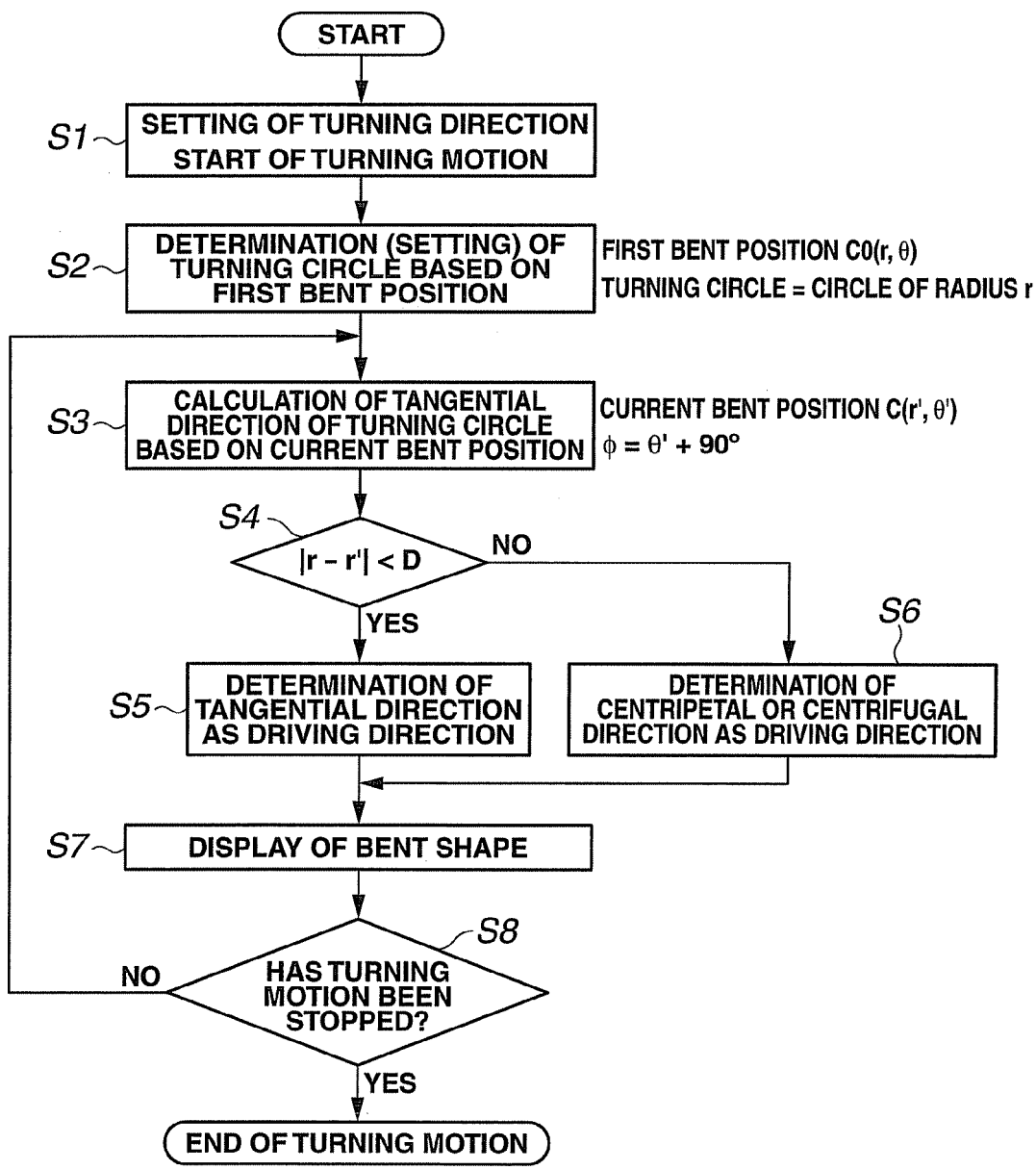
FIG. 5 is a flowchart to show a control procedure for turning and inserting the bending portion, according to the first embodiment.

As shown in FIG. 5, in the first step S1, a surgeon operates the turning designation section 19 to designate a turning direction, and thereafter turns ON the turning switch 19b thereby starting a turning motion.

Note that it is supposed that the turning direction is designated to be the right direction (clockwise direction) when being seen from the distal end side of the axis L as shown by the arrow in FIG. 3. The surgeon may designate the turning direction to be the left direction as well.

In the next step S2, the bending control section 5 performs the determination (setting) of a turning circle based on an initial bent position (a bent state B0 in the example of FIG. 3) when a turning motion is started. It is noted that in this specification, the bent position is simplifiedly represented meaning the position of the distal end of the bending portion 16.

To be specific, the circle shown by the first bent state B0 in FIG. 3 is determined to be the turning circle as described in FIG. 3. It is noted that the bent shape (the bending direction and bending angle from the neutral position) of any bent state such as bent states B0, B1, and so on is detected by the encoders 57a and 57b as bent shape detection means. In this case, the distance from the axis L to the bent position in the first bent state B0 is the radius r of the turning circle, and the angle $\theta$ to the bent position in the radial direction is determined (with a reference direction, for example, the upward direction of bending as being an angle of 0).

FIG. 6 is an explanatory diagram of a turning in the case where the distal end of the bending portion 16 is seen from the distal end side of the axis L in FIG. 3 in the coordinate system of pulley angle (or bending angle). As shown in FIG. 6, let the first bent position be C0(r, $\theta$). Let the distance from the neutral position in this case (that is, where the vertical and horizontal pulley angles are 0) to C0 be the radius r (turning radius) of the turning circle, and let the angle formed between the upward direction and the radius r be $\theta$.

It is noted that although radius r in the pulley angle coordinate system is not consistent with radius r shown in FIG. 3 in a strict sense, the two can be converted to each other as described below, and a notation which does not distinguish the both is used for simplicity in this specification.

As described above, the pulley angle can be regarded as equal to the bending angle of the bending portion 16. Moreover, the turning radius in the coordinate system of the pulley angle corresponds to the turning radius of the distal end of the bending portion 16 in a predetermined relationship.

Therefore, measuring the radius r of the distal end of the bending portion 16 and the rotational position of the pulley for each endoscope, and preparing that information as a correspondence table in a memory and the like, it is possible to convert the radius of a turn that the surgeon wants to make into a turning radius in the pulley angle, or conversely convert a turning radius in the pulley angle into a turning radius of the distal end of the bending portion 16.

Hereafter, description will be made in terms of the pulley angle coordinate system. In step S3, which is a short time after step S2, the bending control section 5 calculates a tangential direction of a turning circle based on a bent position with that time being as present. That is, letting the current bent position be C(r', θ') as shown in FIG. 6, a tangential direction is calculated (by calculating φ=θ'+90° as shown in FIG. 5).

Then, in the next step S4, the bending control section 5 determines whether or not |r−r'| is within a reference value D. That is, the bending control section 5 determines whether or not a condition of |r−r'|<D is satisfied.

It is noted that the reference value D has been set to be an appropriate value corresponding to the operation to make the distal end of the bending portion 16 trace a trail of a turning circle of a radius r. For example, decreasing the value of the reference D enables the turning substantially at a radius of r. The value of the reference value D may be configured to be variably set by an operator such as a surgeon, etc.

The bending control section 5 proceeds to step S5 if the determination result indicates that the condition |r−r'|<D is satisfied, and proceeds to step S6 if the determination result indicates that the condition is not satisfied.

In step S5, (the determination section 5a of) the bending control section 5 determines the tangential direction calculated in step S3 to be a driving direction in which the distal end of the bending portion 16 is to be moved. Then, the bending control section 5 drives bending of the bending portion 16 in the determined driving direction.

In the next step S7, the bending section 5 outputs information of the current bent position, which is detected by the encoders 57a and 57b as bent shape detection means, to a bending portion shape generation circuit 37c of the video circuit 37. The bending portion shape generation circuit 37c generates a video signal of the current bent shape of the bending portion 16, and outputs it to the monitor 10. The current bent shape is displayed on the display screen of the monitor 10.

The surgeon can recognize the bent shape during turning motion from the bent shape displayed on the monitor 10.

After the processing of step S7, the process proceeds to step S8. In step S8, the bending control section 5 determines whether or not an instruction operation to stop the turning motion has been performed by the surgeon. To be specific, it determines whether or not the turning switch 19b of the turning designation section 19 is turned OFF. When the switch is not turned OFF, the process returns to the processing of step S3, and when turned OFF, the process ends the processing of FIG. 5.

On the other hand, when the condition of the inequality is not satisfied, in step S4, the bending control section 5 sets the centripetal or the centrifugal direction as the driving direction to move the distal end of the bending portion 16. Then, the bending control section 5 drives bending of the bending portion 16 in the set driving direction.

It is noted that in this step S6, driving is performed with the centripetal direction being set as the driving direction when r'−r>D, and with centrifugal direction being set as the driving direction when r−r'<D. After step S6, the process proceeds to step S7.

By performing such control, the bending control section 5 can cause the distal end of the bending portion 16 to turn at a radius r (without the insertion portion 11 being twisted in the axial direction) corresponding to the bending angle when turning motion is started by the turning designation section 19. Thus, although in the conventional example described above, twisting operation has been performed as a manipulation for insertion into the deep side of the large intestine, performing the turning motion of the present embodiment in place of that manipulation allows easier insertion of the insertion portion 11 into the deep side of the large intestine.

In the present embodiment, it is possible to maintain the viewpoint of the image pickup unit 31 unchanged when a turning motion is performed, as described later.

The left figure of FIG. 7 schematically shows the viewpoints of the CCD 33 which makes up the image pickup unit 31, by triangles at typical positions when a turning motion is performed according to the present embodiment. In the present embodiment, as shown in the left side of FIG. 7, the direction of viewpoint (specifically, the upward direction of a picked up image of the CCD 33) or the display direction of an endoscope image displayed on the monitor 10 will not change when a turning motion is performed.

In contrast to this, in a conventional example, the viewpoint changes according to the amount of twisting (twisting angle), since twisting is introduced as shown in the right side of FIG. 7.

For example, in the state where the CCD in the right side of FIG. 7 is in the upward direction, if twisting is made by 90° in the right direction, the state in which the CCD is in the upward direction also changes into the lateral direction simultaneously with twisting operation. Moreover, since the upward direction which serves as a reference when an endoscope image is displayed is matched to the direction of the CCD, the endoscope image will have rotated to the lateral direction.

For this reason, it will become difficult for a surgeon to grasp the direction which is actually observed from an endoscope image. It is noted that in the case where twisting is made in the left direction as well, the upward direction of the CCD will become the lateral direction thereof simultaneously with the twisting operation.

In contrast to this, since in the present embodiment, the direction of viewpoint will not change even when turning motion is performed, an endoscope image displayed on the monitor 10 will not be rotated by a turning motion. Therefore, a surgeon will be freed from the problem that grasping the observation direction becomes difficult. Moreover, while the amount of twisting is limited since twisting is performed in a conventional example, the present embodiment will not be limited by the amount of turning during turning motion, the amount of turning can be increased as much as desired by increasing the number of rotations of turning.

So far, description has been made using the viewpoint, description utilizing the bending direction of bending portion 16 will be as follows. Suppose that the upward direction of the CCD in the left side of FIG. 7 is set to be for example the upward direction in the bending direction of the bending portion 16 (shown as the upward direction of bending in brackets in FIG. 7). In this case, similarly with the case of the upward direction of CCD, the orientation of the upward direction in the bending direction of the bending portion 16 will not be rotated maintaining the same orientation (the orientation of the upward direction in FIG. 7), when a turning motion is performed. Although description has been made for the case of the upward direction as a specific example, other bending directions in the bending portion 16 will also not change its orientation during turning motion.

Therefore, in the present embodiment, the electric motors 55a and 55b, which make up bending driving means, can cause the bending portion 16 to make a turning motion substantially without rotation of the orientation of each bending direction of the bending portion 16.

In contrast to this, in the case of a conventional example in the right side of FIG. 7, the orientation of the bending portion will be changed as expected from the fact that twisting is performed.

For this reason, in the conventional example, when twisting operation is performed, it becomes difficult to grasp actual bending direction of the bending portion in a body cavity. In contrast to this, since in the present embodiment, the actual direction of bending direction will not change even when a turning motion is performed, it is possible to maintain a state in which a bending operation is easily performed.

Thus, according to the present embodiment, it is possible to perform smooth insertion into a curved site such as a large intestine while maintaining a state in which observation is easy. Moreover, a surgeon can perform smooth insertion into a curved site such as a large intestine by simple operation through the operation of the turning designation section 19.

Moreover, since it is configured such that the state of bent shape of the bending portion 16 during turning motion is displayed, a surgeon can visually confirm the turning motion.

[Second Embodiment]

Next, a second embodiment of the present embodiment will be described. The configuration of the present embodiment is the same as that of the first embodiment. However, in the present embodiment, the turning designation section 19 is configured to be able to perform the designation of a turning speed, as well as the designation of a turning direction.

Figure 8:
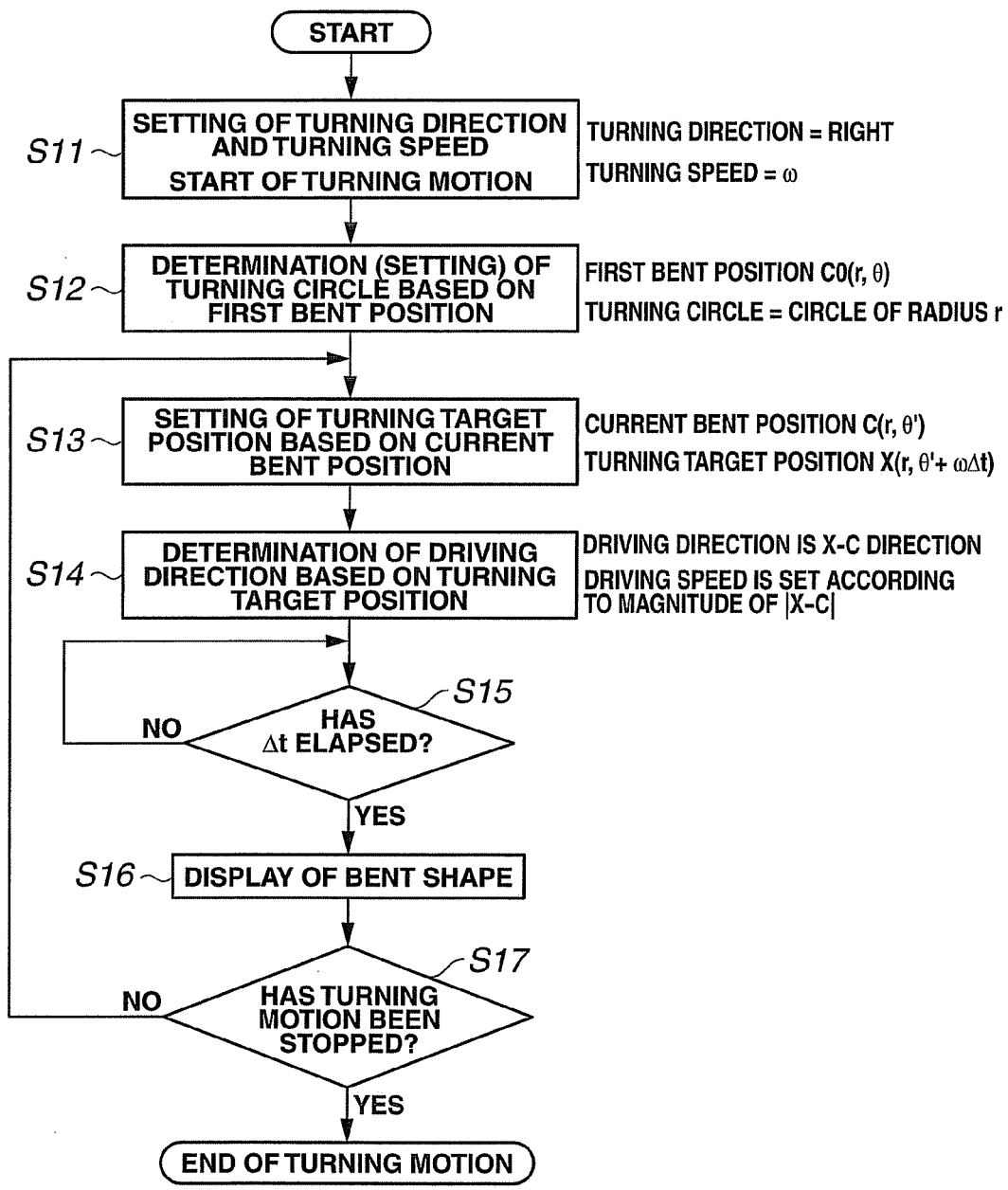
FIG. 8 is a flowchart to show a control procedure for turning and inserting the bending portion, according to a second embodiment of the present invention.

Next, the operation of the present embodiment will be described with reference to FIG. 8. FIG. 8 shows an example of the control procedure to cause a turning motion in the present embodiment.

When the power supply of the endoscope apparatus 1 is turned on and its operation has started, in the first step S11, a surgeon operates the turning designation section 19 to designate a turning direction and a turning speed, and thereafter starts a turning motion. Now suppose that the surgeon has designated the turning direction to be right direction, and the turning speed to be ω.

Then, in the next step S12, the bending control section 5 performs the setting of a turning circle based on the current bent position. The current bent position is set, for example, to C0(r, θ) and the turning circle is set to a circle of radius r.

The setting of a turning target position X is performed with the time of step S13 after a short time from step S12 being as the current time. Although, in the first embodiment, the tangential direction is adopted as the turning target position, in the present embodiment, the turning target position X is supposed to be a turning target position in which the radius is r, and radial angle θ' of the current bent position is θ'+ωΔt.

Figure 9:
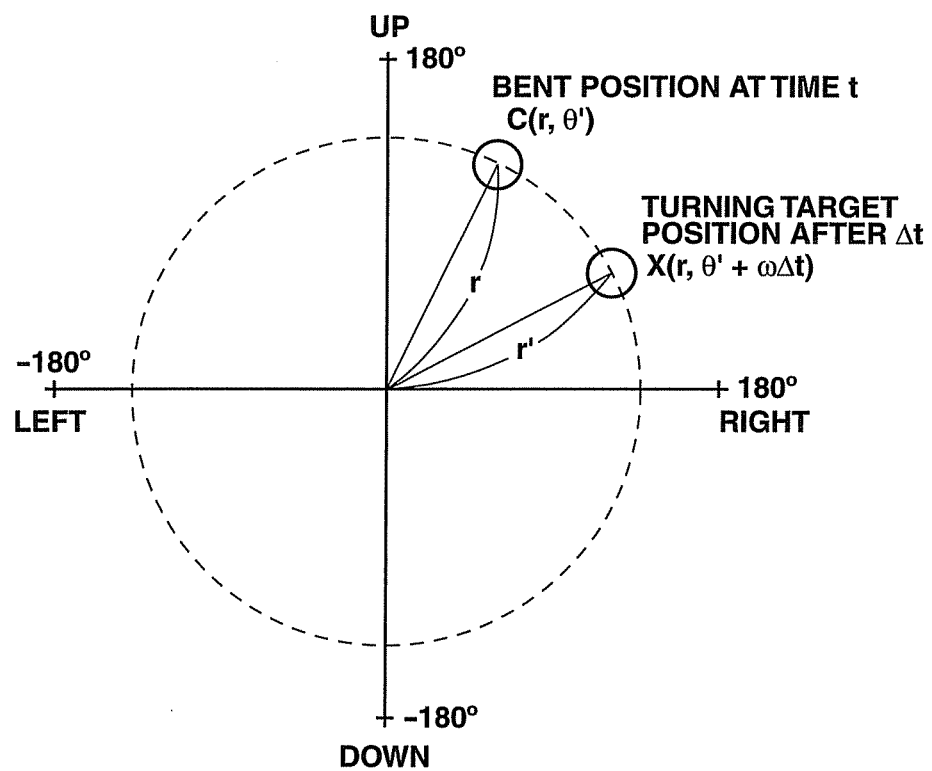
FIG. 9 is an explanatory diagram of the case where the bending portion is turned.

FIG. 9 is an explanatory diagram of step S13. In FIG. 9, when it is supposed that the bent position at time t is C(r, θ'), a turning target position X after Δt from the time t is set.

The turning target position X is set as (r, θ'+ωΔt). In the next step S14, the determination section 5a of the bending control section 5 determines a driving direction based on the turning target position X. In this case, the driving direction will be the direction from the bent position of step S13 to the turning target position X. That is, let C and X be vectors, the direction of a vector X−C will the driving direction. The driving speed will be determined according to the magnitude of |X−C|.

Then, in the next step S15, the bending control section 5 determines if a predetermined time Δt has elapsed. When the predetermined time Δt has not elapsed, the passage of this time is waited. In this case, operation of driving to the turning target position X is performed.

On the other hand, when the predetermined time Δt has elapsed, the process proceeds to the processing of step S16. In step S16, the bending control section 5 outputs information of the current bent position detected by the encoders 57a and 57b to the bending portion shape generation circuit 37c of the video circuit 37. The bending portion shape generation circuit 37c generates a video signal of a current bent shape of the bending portion 16 and outputs it to the monitor 10. The current bent shape is displayed on the display screen of the monitor 10.

The surgeon can recognize a current bent shape from the bent shape displayed on the monitor 10. In that case, a turning speed can also be confirmed.

In the next step S17, the bending control section 5 determines whether or not the instruction operation to stop turning motion has been performed. When the determination result indicates that the instruction operation has not been performed, the process returns to the processing of step S13, and a next turning target position will be set at that bent position, thereafter repeating the above described operation.

On the other hand, when an instruction operation to stop turning motion has been performed in the determination processing of step S17, the bending control section 5 ends the control operation of FIG. 8.

According to the present embodiment, as with the first embodiment, it is possible to turn the distal end of the bending portion 16 with simple operation and smoothly insert the insertion portion 11 into a curved site while maintaining a state in which observation is easy.

The present invention further allows the setting of a turning speed when turning is performed. Therefore, a surgeon can make a turning at his or her desired speed.

Further, a surgeon can confirm the bent shape and the state of the turning speed of the bending portion 16 during a turning motion.

[Third Embodiment]

Next, a third embodiment of the present invention will be described. The configuration of the present embodiment is the same as that of the first embodiment. However, in the present embodiment, the turning designation section 19 is configured to allow the designation of turning direction as well as the designation of the magnitude of turning radius.

In the above described first and second embodiment, when a turning motion is started by the turning designation section 19, (a value of) the radius determined from the position of the distal end of the bending portion 16 at the start is set as the turning radius for the turning.

In contrast to this, in the present embodiment, it is configured such that the turning radius can be set to a radius different from the radius determined from the position of the distal end of the bending portion 16 at the start of starting a turning motion thereby causing a turning motion to be performed.

Therefore, in the present embodiment, when starting a turning motion, the bending control section 5 performs the control to acquire information of (the radius determined from) the position of the distal end of the bending portion 16 at the start, as described below, and to move the distal end to a position of the turning radius that has been set by instruction, thereafter performing the control to cause a turning motion at the turning radius.

Figure 10:
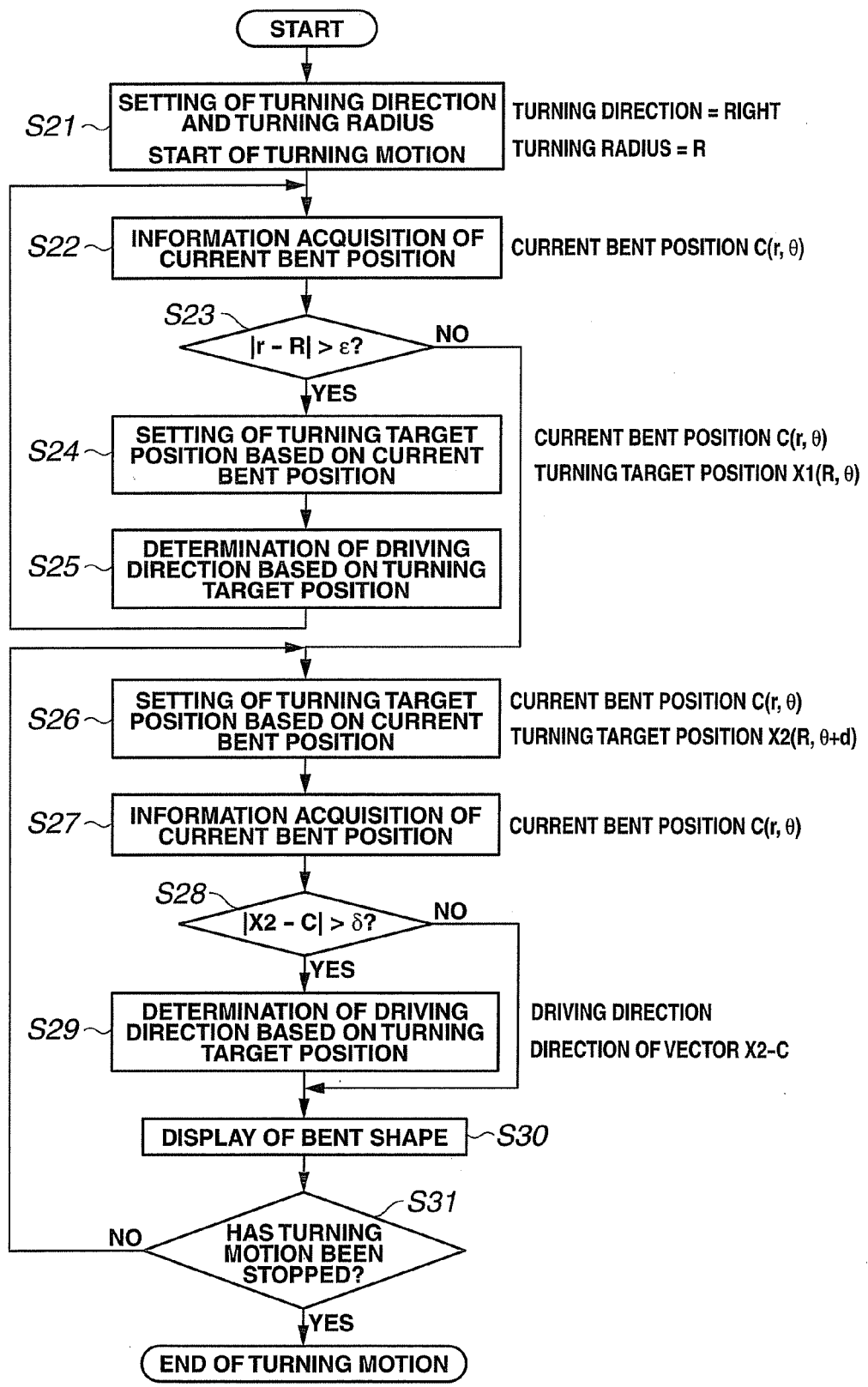
FIG. 10 is a flowchart to show a control procedure for turning and inserting the bending portion, according to a third embodiment of the present invention.

Next, the operation of the present embodiment will be described with reference to FIG. 10. FIG. 10 shows an example of the control procedure to cause a turning motion in the present embodiment.

When the power supply of the endoscope apparatus 1 is turned on thereby starting its operation, in the first step S21, a surgeon operates the turning designation section 19 to designate a turning direction and a turning radius, and thereafter starts a turning motion. Now suppose that the surgeon has designated the turning direction to be the right direction, and the turning radius to be R.

Then, in the next step S22, the bending control section 5 acquires the information of the current bent position via the encoders 57a and 57b. Suppose that, for example, the bent position acquired in step S22 is $C(r, \theta)$ as shown in FIG. 11.

In the next step S23, the bending control section 5 determines whether or not the absolute value of the difference between the radius of a current bent position and a designated turning radius R is larger than a predetermined value $\epsilon$. That is, the bending control section 5 determines whether or not the condition of $|r-R|>\epsilon$ is satisfied.

Figure 11:
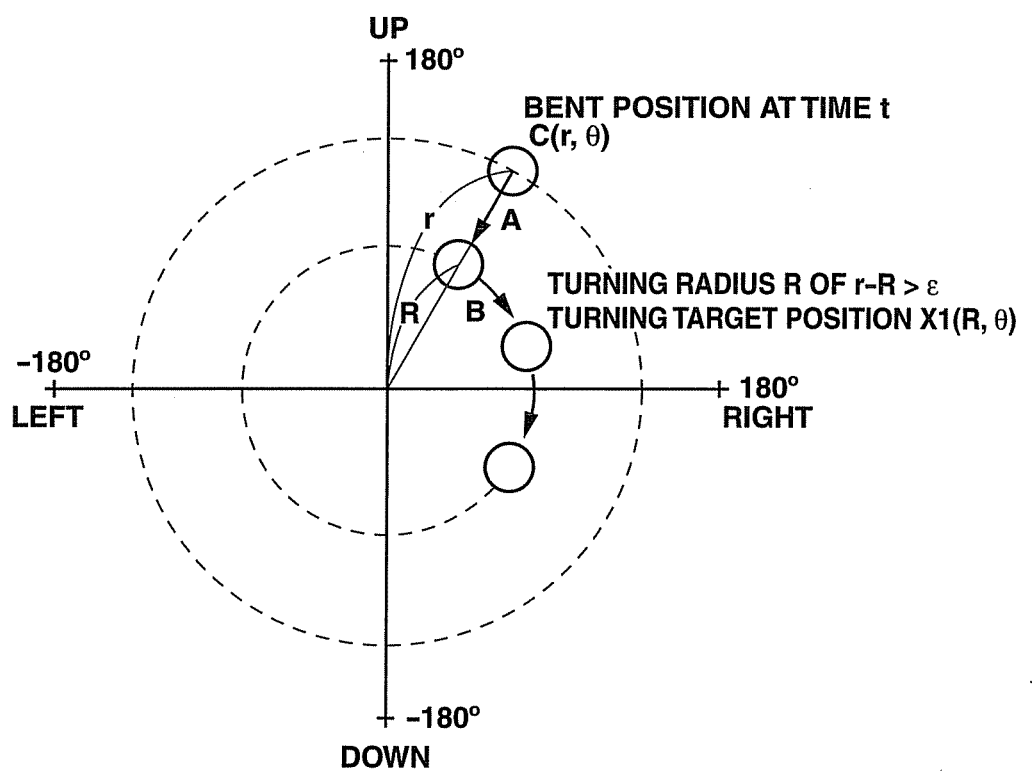
FIG. 11 is an explanatory diagram of the case where the bending portion is turned.

FIG. 11 shows an example in which a turning radius R when the above described condition is satisfied is set. Letting the bent position at time t be $C(r, \theta)$, a turning radius R, which satisfies $r-R>\epsilon$, is set inside thereof.

In this case, in the next step S24, the bending control section 5 performs the setting of a turning target position X1 based on a current bent position. To be specific, the turning target position X1 is set to be $X1(R, \theta)$.

After this setting, in the next step S25, the bending control section 5 determines a driving direction based on the turning target position X1. To be specific, the bending control section 5 controls the bending angle to be changed by a predetermined amount with reference to a detection signal by the encoders 57a and 57b as bent shape detection means, and thereafter returns to the processing of step S22.

In the example shown in FIG. 11, the bending angle is changed in the direction shown by a thick arrow A. In this way, by repeating the processing of steps S22 to S25, it is possible to set r of the current bent position $C(r, \theta)$ to be a value close to R. Therefore, in this case, the determination will be such that the condition of $|r-R|>\epsilon$ shown in step S23 is not satisfied, that is, $|r-R|\leq\epsilon$.

In the case of this determination result, the process proceeds to step S26, and in this step S26, the bending control section 5 performs the setting of the turning target position X2 based on a current bent position. The bending control section 5 sets the turning target position X2 $(R, \theta+d)$ for the current bent position $C(r, \theta)$.

In the next step S27, the bending control section 5 acquires information of the current bent position. In this case, the radius r of the bent position $C(r, \theta)$ will be closer to the turning radius R.

In the next step S28, the bending control section 5 determines whether or not the absolute value of the difference between the turning target position X2 and the current bent position C is larger than a predetermined value $\delta$. That is, the bending control section 5 performs the determination of $|X2-C|>\delta$.

When the determination result indicates the satisfaction of the above described inequality, in step S29, the bending control section 5 determines the driving direction based on the turning target position X2.

To be specific, letting the turning target position X2 and the bent position C be vectors, a vector direction of X2-C is determined to be the driving direction. In FIG. 11, it is determined that for example, the driving direction be the tangential direction of radius r of the current bent position C as shown by an arrow B (or $\theta$ be increased while maintaining the radius r).

After the above described determination, the bending control section 5 performs the control to move the current bent position in the driving direction through a motor driving section 56, thereafter proceeding to the next step S30.

On the other hand, when the determination result indicates the dissatisfaction of $|X2-C|>\delta$ in step S28, that is, when it can be considered that the current bent position C is close to the turning target position X2, the process proceeds to step S30.

In step S30, the bending control section 5 outputs information of the current bent position detected by the encoders 57a and 57b to the bending portion shape generation circuit 37c of the video circuit 37. Then, the bending control section 5 causes a current bent shape to be displayed on the display screen of the monitor 10.

A surgeon can recognize the bent shape including the magnitude of turning radius, of the bending portion 16 during bending operation from the bent shape displayed on the monitor 10. In the next step S31, the bending control section 5 determines whether or not an instruction operation to stop the turning motion has been performed.

When the determination result indicates that the instruction operation has not been performed, the process returns to the processing of S26, and the information of bent position at that time is acquired, and a next turning target position X2 at that time is set to repeat the above described operation.

On the other hand, when an instruction operation to stop turning motion has been performed in the determination processing of step S31, the bending control section 5 ends the turning operation that causes turning of the bending portion 16 of FIG. 10.

The present embodiment has similar effects to those of the first embodiment. Moreover, the present embodiment allows the setting of a turning radius when further causing turning. Therefore, a surgeon can cause a turning at his or her desired turning radius.

It is noted that as a variation of the present embodiment, it may be configured such that a turning speed can be set as with the second embodiment.

Figure 12:
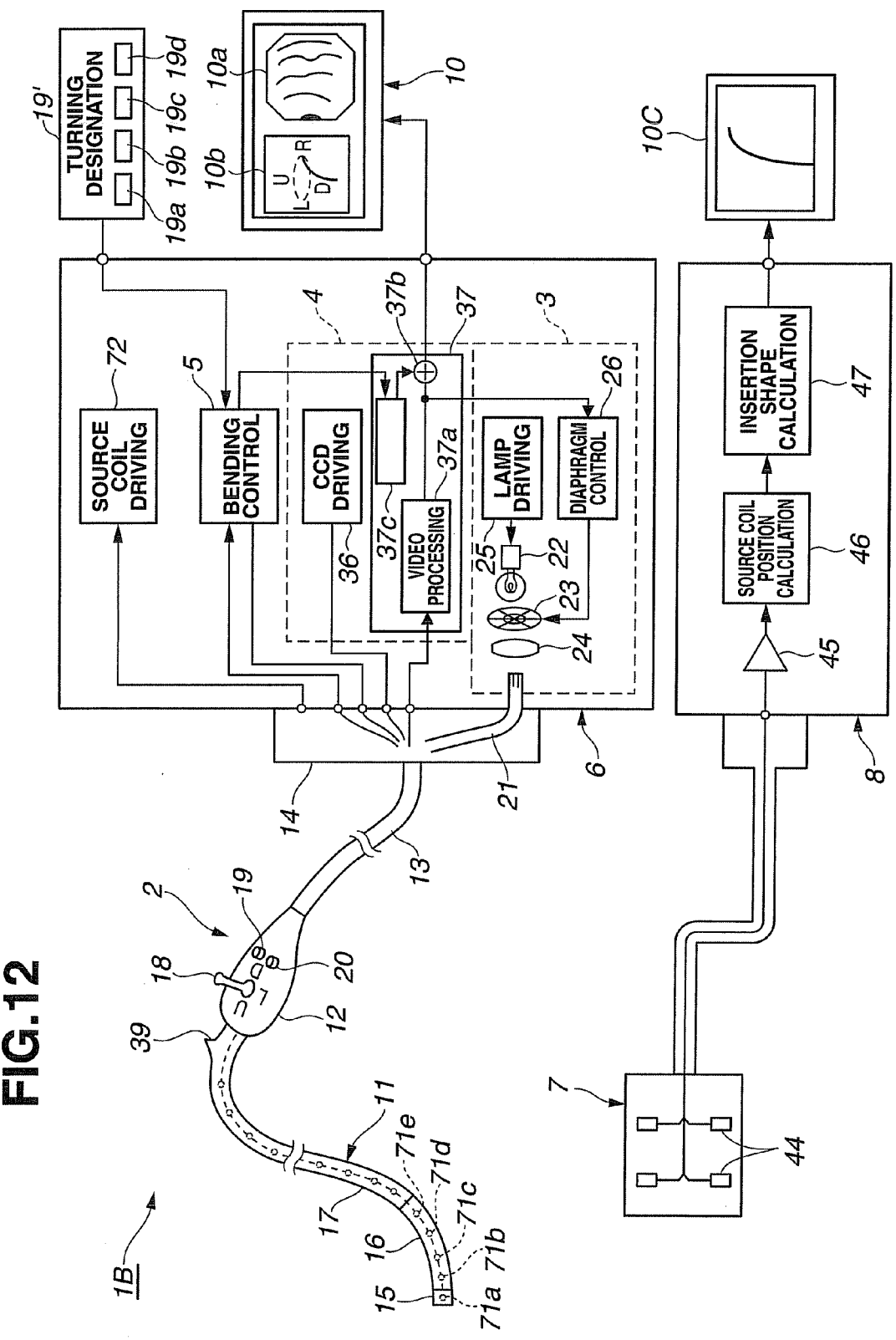
FIG. 12 is a diagram to show the general configuration of an endoscope apparatus of a variation of the third embodiment of the present invention.

Moreover, the present embodiment will not be limited to the case of the endoscope apparatus 1 having the configuration shown in FIG. 1, and may have a configuration as shown in FIG. 12.

An endoscope apparatus 1B shown in FIG. 12 is configured such that in the endoscope apparatus 1 including the endoscope 2 shown in FIG. 1, N source coils 71a, 71b, . . . and 71n are disposed as position detection elements at a predetermined interval within the insertion portion 11 in the longitudinal direction thereof in the endoscope 2.

Those source coils 71a, 71b, . . . and 71n are connected with a source coil driving section 72 provided within the processor 6, and the source coil driving section 72 successively applies a coil driving signal of alternating current (AC) to the source coils 71a, 71b, . . . and 71n. As a result of this, an AC magnetic field is generated in the periphery of each source coil provided within the insertion portion 11.

Moreover, a sense coil unit 7 that detects the AC magnetic fields generated at the source coils 71a, 71b, . . . and 71n is disposed at a predetermined position in a bed not shown on which a patient to be subjected to insertion of the endoscope 2 is placed, and is connected with an endoscope shape detection apparatus 8.

The sense coil unit 7 includes a group of sense coils 44 that respectively detect magnetic fields emitted from N source coils 71a, 71b, . . . and 71n provided within the insertion portion 11, and output as a magnetic field detection signal.

The endoscope shape detection apparatus 8 includes: an amplifier 45 that amplifies a magnetic field detection signal outputted from the sense coil unit 7; a source coil position calculation section 46 that detects 3-dimensional coordinate positions of N source coils 71a, 71b, . . . and 71n based on the magnetic field detection signal outputted from the amplifier 45; and an insertion shape calculation section 47 that calculates an insertion shape of the insertion portion 11 based on the insertion shape information outputted from the source coil position calculation section 46, and outputs it as an insertion shape image signal.

The insertion shape image signal outputted from the insertion shape calculation section 47 is outputted on the monitor 10C, and an insertion shape image of the insertion portion 11 is displayed on the display screen of the monitor 10C.

When an endoscope apparatus 1B of the variation shown in FIG. 12 is used, it is possible to insert the insertion portion 11 of the endoscope 2 into a body cavity while observing the insertion shape thereof. Therefore, it becomes easier for a surgeon to perform insertion into a body cavity.

Further, the endoscope apparatus 1B shown in FIG. 12 is provided with a turning designation section 19', which performs various designations in turning motion at the side of the processor 6, and the signal designated thereby is inputted into the bending control section 5.

The turning designation section 19' is provided with: a direction switch 19a for designating a turning direction; a turning switch 19b for starting/stopping a turning motion; a speed designation switch 19c for designating a turning speed; and a radius designation switch 19d for designating the radius of a turning circle.

The direction switch 19a and the turning switch 19b are similar to those described in the first embodiment, and the speed designation switch 19c is provided with a plurality of switches corresponding to a plurality of turning speeds respectively, so that an operator such as a surgeon, etc. turns on a switch corresponding to one turning speed out of a plurality of turning speeds to designate the speed.

Moreover, the radius designation switch 19d is provided with a plurality of switches corresponding to a plurality of radii respectively, and an operator turns on a switch corresponding to one radius out from a plurality of radii to designate the radius.

Therefore, an operator can designate a turning direction, a turning speed, a radius of turning circle, and the like by operating the turning designation section 19'.

Further, when one designates the turning direction, the turning speed, and the radius of turning circle through the turning designation section 19' and causes a turning motion, one can confirm the turning direction, the turning speed, and the radius of the turning circle during turning motion by the monitor 10.

Note that besides the above described embodiments, it may be configured such that the information for operating a joystick 18 so as to make a turning motion is prerecorded as turning designation information in a recording portion and the like, so that the operator performs designation operation to drive the bending of the bending portion 16 with the electric motors 55a and 55b as the bending driving means according to the recorded turning designation information, thereby causing the bending portion 16 to make a turning motion.

It is noted that although in the above described embodiments, description has been made on an example in which joystick motors 58a and 58b are provided, a rotatable roller may be provided in place of the joystick motors 58a and 58b, respectively. Moreover, configuration may be such that the rotational angle of each roller is detected by the encoders 59a and 59b.

Further, embodiments which are configured by partially combining the above described each embodiment also belong to the present invention.

What is claimed is:

1. An endoscope apparatus, comprising:
an insertion portion that is inserted into a subject;
a bending portion provided on a distal end side of the insertion portion, the bending portion being bendable and turnable centering around an insertion axis of the insertion portion;
a bending driving section that drives bending of the bending portion with respect to the insertion axis;
a bending driving control section that controls a bending driving status of the bending driving section based on a control signal to be inputted;
a bending direction changing section that detects bending driving information showing a bent state of the bending portion according to control of the bending driving control section and, with the bent state maintained, outputs the control signal to the bending driving control section, the control signal adapted to continuously change a bending direction of the bending portion by controlling the driving of the bending driving section such that a distal end of the bending portion makes a turning motion forming a circular trail centering around the insertion axis, the bending portion maintaining the bent state;
a bending instruction operation section for performing an instruction operation to bend the bending portion in vertical and horizontal directions;
a turning designation section for designating the turning motion to turn a distal end side of the bending portion with respect to a proximal end of the bending portion, the turning designation section being provided at a position different from a position where the bending instruction operation section is provided;
a direction switch for designating a turning direction of the turning motion by a switch operation, the direction switch being provided at the turning designation section; and
a turning switch for starting/stopping the turning motion by a switch operation, the turning switch being provided at the turning designation section;
wherein the bending driving control section further comprises a turning circle determination section that determines a turning circle having a radius to be a distance from the insertion axis to the distal end of the bending portion when the turning switch is operated to start the turning motion, and a tangential direction calculation section that calculates a tangential direction of the turning circle determined by the turning circle determination section,
wherein, when the bending instruction operation section is operated for instruction, the bending driving control section controls the bending driving of the bending driving section in response to the instruction operation of the bending instruction operation section; and
wherein, when the turning switch is operated to start the turning motion, the bending driving control section controls the bending driving of the bending driving section such that the distal end of the bending portion makes the turning motion to draw a circle.

2. The endoscope apparatus according to claim 1, wherein the turning designation section further comprises:
   a radius designation section that designates a turning radius at which to cause the bending portion to make the turning motion, wherein
   the bending driving control section outputs, to the bending driving section, a control signal that drives bending of the bending portion to a bent state corresponding to the turning radius.

3. The endoscope apparatus according to claim 2, wherein the turning radius is a distance from the insertion axis to the distal end of the bending portion when the bending portion is bent.

4. The endoscope apparatus according to claim 2, wherein the turning designation section further comprises a turning speed designation section for designating a turning speed of the turning motion.

5. The endoscope apparatus according to claim 4, wherein the bending direction changing section controls the bending portion so as to make the turning motion without being rotated about the insertion axis.

6. The endoscope apparatus according to claim 5, wherein the turning radius at which to cause the bending portion to make the turning motion is determined from the bending angle of the bending portion according to the bending driving information, and the bending driving section is driven so as to cause the bending portion to make the turning motion based on the determined turning radius and the turning direction.

7. The endoscope apparatus according to claim 6, further comprising:
   an insertion portion shape calculation section that calculates an insertion portion shape of the insertion portion including the bending portion, wherein
   the calculated insertion portion shape can be displayed by a display apparatus.

8. The endoscope apparatus according to claim 6, further comprising:
   a signal processing portion that performs signal processing for an image pickup device provided in the distal end of the insertion portion, and generates a video signal to be displayed as an endoscope image; and
   a bent shape detection section that detects a bent shape of the bending portion, wherein
   the endoscope image and the bent shape of the bending portion during the turning motion can be adjacently displayed on a display surface of the same display apparatus.

9. The endoscope apparatus according to claim 4, further comprising:
   a signal processing portion that performs signal processing for an image pickup device provided in the distal end of the insertion portion, and generates a video signal to be displayed as an endoscope image; and
   a bending portion shape generation section that generates a video signal to represent a bent shape of the bending portion, wherein
   the endoscope image and the bent shape of the bending portion during the turning motion can be adjacently displayed on a display surface of the same display apparatus.

10. The endoscope apparatus according to claim 1, further comprising a bending portion shape generation section that generates a video signal to represent a bent shape of the bending portion, wherein the bent shape of the bending portion during the turning motion can be displayed by a display apparatus.

11. The endoscope apparatus according to claim 1, wherein the bending direction changing section controls the bending portion so as to make the turning motion without being rotated about the insertion axis.

12. The endoscope apparatus according to claim 11, wherein the turning radius at which to cause the bending portion to make turning motion is determined from a bending angle of the bending portion according to the bending driving information, and the bending driving section is driven so as to cause the bending portion to make the turning motion based on the determined turning radius and the turning direction.

13. The endoscope apparatus according to claim 1, wherein the bending driving control section further comprises a driving direction determination section that determines a driving direction in which the bending portion is bent to be the tangential direction calculated by the tangential direction calculation section.

14. The endoscope apparatus according to claim 1, wherein the bending driving control section further controls the bending driving of the bending driving section so as to satisfy a condition that an absolute value of a difference between a present position of the distal end of the bending portion and the radius determined by the turning circle determination section is less than a reference value.

15. The endoscope apparatus according to claim 1, wherein the bending driving control section controls the bending driving of the bending driving section such that the distal end of the bending portion turns clockwise or counterclockwise in response to the switch operation of the direction switch.

* * * * *